United States Patent [19]

Zoeller et al.

[11] Patent Number: 4,761,496
[45] Date of Patent: Aug. 2, 1988

[54] ALKYLENE AND DIAKYL KETALS AND ALKYL ALPHA-ENOL ETHERS OF ALPHA-ACETYL CINNAMIC ACIDS AND ESTERS THEREOF

[75] Inventors: Joseph R. Zoeller; Charles E. Sumner, Jr., both of Kingsport, Tenn.

[73] Assignee: Eastman Kodak Company, Rochester, N.Y.

[21] Appl. No.: 107,742

[22] Filed: Oct. 13, 1987

[51] Int. Cl.$^4$ .............................................. C07C 69/76
[52] U.S. Cl. .................................... 560/60; 560/9; 562/426; 562/459; 549/347; 549/369; 549/430
[58] Field of Search ...................... 560/60, 9; 582/426, 582/459; 549/347, 369, 430

[56] References Cited

U.S. PATENT DOCUMENTS 4,081,476  3/1978  Anderson et al. .................... 560/60
4,621,150  11/1986  Hirai et al. ............................. 560/60

FOREIGN PATENT DOCUMENTS

EP44972  3/1982  European Pat. Off. .............. 560/60

Primary Examiner—Paul J. Killos
Attorney, Agent, or Firm—Charles R. Martin; William P. Heath, Jr.

[57] ABSTRACT

An alkylene or dialkyl ketal of the formula

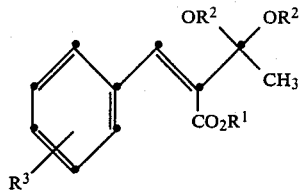

wherein
$R^3$ is halo, carboxy or $(C_1-C_{12})$alkyl, alkoxy, acyl, acyloxy, carbalkoxy or alkylthio.
$R^1$ is $(C_1-C_{12})$alkyl, $(C_6-C_{20})$aryl or $(C_7-C_{21})$alkylaryl or aralkyl; and
$R^2$ is $(C_1-C_{12})$alkyl or the two $R^2$ taken together are $(C_2-C_{12})$alkylene.

An alpha-enol ether of the formula

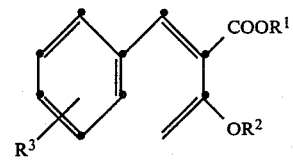

wherein
$R^1$ and $R^3$ are as defined above and $R^2$ is $(C_1-C_{12})$alkyl.

21 Claims, No Drawings

ALKYLENE AND DIAKYL KETALS AND ALKYL ALPHA-ENOL ETHERS OF ALPHA-ACETYL CINNAMIC ACIDS AND ESTERS THEREOF

BACKGROUND OF THE INVENTION

1. Field of the Invention

The present invention relates to novel compositions of matter encompassing alkylene and dialkyl ketals and alkyl alpha-enol esters of alpha-acetyl cinnamic acids and esters thereof. The ketals and alpha-enol ethers of the invention are useful for the synthesis of 2-naphthanoic acids having a specific substitution pattern and esters thereof.

2. Description of the Prior Art

Ketals and alpha-enol ethers of alpha-acetyl cinnamic acid and esters thereof are useful for the synthesis of substituted 2-naphthanoic acids and esters thereof which are polymer intermediates. One of the major problems posed by the synthesis of 2-napthanoic derivatives useful as polymer intermediates is that a second functional group in addition to the carboxyl group must be present. Moreover, such functional groups must be present at a specific location on the molecule. Thus, in turn, the precursor ketals and alpha-enol ethers must also be substituted at specifc sites on the aromatic ring. The development of such specific site substituted ketals and alpha-enol ethers thereof is of great significance to the industry.

Accordingly, there is a definite need for alkylene and dialkyl ketals and alpha-enol ethers of alpha-acetyl cinnamic acids and esters thereof having a specific substitution pattern.

SUMMARY OF THE INVENTION

This invention relates to an alkylene or dialkyl ketal of the formula

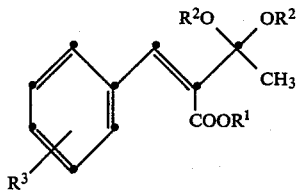

wherein
$R^1$ is $(C_1-C_{12})$alkyl, $(C_6-C_{20})$aryl, or $(C_7-C_{21})$alkylaryl or aralkyl;
$R^2$ is $(C_1-C_{12})$alkyl or the two $R^2$ taken together are $(C_2-C_{12})$alkylene; and
$R^3$ is halo, carboxy or $(C_1-C_{12})$alkyl, alkoxy, acyl, acyloxy, carbalkoxy or alkylthio.

In addition, this invention also relates to an alpha-enol ether of the formula

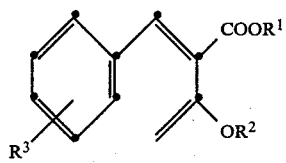

wherein
$R^1$ and $R^3$ are as defined above and $R^2$ is $(C_1-C_{12})$alkyl.

A more complete appreciation of the invention and many of the attendant advantages thereof will be readily perceived as the same becomes better understood by reference to the following detailed description of the preferred embodiments thereof.

DESCRIPTION OF THE PREFERRED EMBODIMENTS

In one aspect of the invention, the composition of matter provided is a novel alkylene or dialkyl ketal of the formula

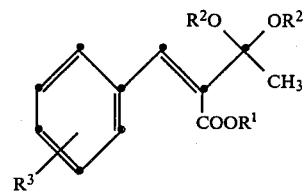

wherein
$R^1$ is $(C_1-C_{12})$alkyl, $(C_6-C_{20})$aryl, or $(C_7-C_{21})$alkylaryl or aralkyl;
$R^2$ is $(C_1-C_{12})$alkyl or the two $R^2$ taken together are $(C_2-C_{12})$alkylene; and
$R^3$ is halo, carboxy or $(C_1-C_{12})$alkyl, alkoxy, acyl, acyloxy, carbalkoxy or alkylthio.

The $R^3$ substituent of the aromatic ring may be in the ortho, meta or para position with respect to the carboxy containing substituent. A preferred group of alkylene and dialkyl ketals of the invention is that wherein the $R^3$ of the aromatic ring is in the ortho or para position, and more preferably in the para position. Preferred $R^3$ substituents are alkyl, halo, carboxy, acyl and alkoxy. Among these, preferred are methyl, ethyl, isopropyl, chlorine, bromine, methoxy, ethoxy and acetyl. Another group of preferred ketals of the invention is that wherein the $R^1$ substituent is $(C_1-C_5)$alkyl, $(C_6-C_{10})$aryl or $(C_7-C_{11})$alkylaryl or aralkyl, and even more preferred is a group of ketals wherein the $R^1$ substituent is methyl, since most of the methyl ester derivatives are volatile and therefore easier to isolate than the higher alkyl or aryl esters.

Another group of preferred ketals of the invention are those where in the $R^1$ substituent is $(C_1-C_5)$alkyl, and most preferably methyl. Still another group of preferred ketals of the invention is that wherein the two $R^2$ substituents form a $(C_2-C_3)$alkylene, and more preferably ethylene.

The ketals of the invention can be prepared by reacting an alpha-acetyl cinnamic acid or ester thereof of the formula

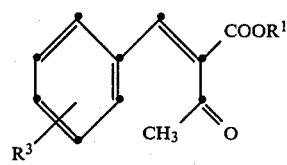

wherein $R^1$ and $R^3$ are as defined above with a ketalizing agent selected from the group consisting of alkyl glycols, dialkyl ketals and trialkyl orthoesters in the presence of an acid catalyst and preferably in the further presence of a transition metal catalyst. The cinnamic acid or ester thereof and the ketalizing agent are reacted in proportions and under reaction conditions effective to form the ketal. This process, the reaction condition catalysts, and the reactants necessary for conducting the process are disclosed in pending U.S. application Ser. No. 107,744, filed Oct. 13, 1987, by the present inventors, the content of which is incorporated herein by reference. In brief, the ketals of the invention are typically prepared using an acid to the catalyst weight ratio of about 10:1 to 10,000:1, preferably 50:1 to 5,000:1, and a molar equivalent of alpha-acetyl cinnamic acid or ester to the ketalizing agent of about 1:1 to 1:5, preferably 1:1 to 1:3. The reaction is preferably conducted at a temperature of about 25° to 250° C., and more preferably about 40° to 200° C.

Suitable ketalizing agents are alkyl glycols, dialkyl ketals and trialkyl orthoesters such as 1,2- and 1,3-($C_2$–$C_{12}$)glycols, ($C_1$–$C_{12}$)trialkyl orthoesters and ($C_1$–$C_{12}$)dialkyl ketals derived from ($C_1$–$C_{12}$)ketones. Examples of suitable glycols and orthoesters are neopentyl glycol, propanediol, 1,2- and 1,3-ethylene glycol, tri-methyl orthoformate and the like. Preferred are alkyl glycols and alkyl orthoformates having 1 to 12 carbon atoms. Alkyl glycols, dialkyl ketals and tri-alkyl orthoesters are commercially available or may be prepared by methods known in the art.

Illustrative of acid catalyst for use in the ketalization reaction are strong acids such as sulfuric acid, trifluoroacetic acid, hydrochloric acid or sulfonic acid, or an acidic resin such as acid-exchange resins. Any acidic resin known in the art is suitable for use in this invention. By means of example, an acidic resin such as Amberylst 15 ® can be utilized. Acidic resins are commercially available or can be prepared by methods known in the art.

The transition metal catalyst for the ketalization reaction can be any transitional metal olefin isomerization catalyst which isomerizes the unreactive isomer of the ketone reactant into the more reactive isomer and thereby provides a constant supply of reactive ketone. Isomerization catalyst include Group VIII metal catalysts such as rhodium, ruthenium, cobalt or palladium catalysts or derivatives thereof. Examples are cobalt hydride, palladium hydride, carbonyl hydride tris(triphenylphosphine)rodium and hydridochlorocarbonyl tris(triphenylphosphine)ruthenium.

The ketalizing reaction may be conducted in liquid phase and an inert solvent, although not necessary, may be also added. Within the context of the invention, an inert solvent is defined as a solvent which can withstand the reaction temperatures involved in the ketalization reaction without undergoing significant decomposition and interfering with the course of the reaction. Examples of inert solvents are acyclic, cyclic and aromatic hydrocarbons or halides thereof or their azeotropes formed with water, and alcohols and glycols from which the alkylene and alkyl residues of the $R^2$ substituent of the ketals are derived.

The alpha-acetyl cinnamic acids or esters thereof employed in the ketalization reaction can all be prepared by the knoevenagel condensation reaction of aromatic aldehydes with acetoacetic acids or esters thereof which is well known and efficient method for generating alpha-acetyl cinnamic acid esters (Jones, Org. Reactions 15:204 (1967), the content of which is incorporated herein by reference.) Acetoacetic acid and the alkyl esters thereof are commercially available or can be prepared by means known in the art. Examples of the esters are methyl, ethyl and isopropyl esters, among others.

The benzaldehydes to be used as a reactants in the synthesis of the ketones of the invention are known in the art, some are commercially available and all can be prepared by methods known in the art. The aromatic ring of the benzaldehyde may be substituted at the ortho, meta or para position. One group of preferred benzaldehydes which are suitable for use in the preparation of alpha-acetyl cinnamic acids or esters thereof consists of benzaldehydes substituted in the ortho and para position, and preferably those substituted in the para position. Examples of substituents of the aromatic ring of the benzaldehyde are halo such as chlorine or bromine, carboxy, ($C_1$–$C_{12}$)alkyl such as methyl, ethyl or isopropyl, alkoxy such as methoxy or ethoxy, acyl such as acetyl, and the like. Preferred among the substituents are chlorine, bromine, carboxy, methyl, methoxy and acetyl, among others.

In general, when the reaction of the acetoacetic acid or ester thereof or the acetylacetone with the benzaldehyde is conducted to prepare an alpha-acetyl cinnamic acid or ester thereof, the reaction is conducted at a temperature of about 0° to 250° C., and more preferably about 50° to 150° C., and at a pressure of about 0.1 mmHg to 10 atm, and more preferably 1 atm. Although the reactants may be present in any amount, it is preferable that the acetoacetic acid or ester thereof and the benzaldehyde be present in a proportion of about 25:1 to 1:25 and more preferably about 1:1 to 1:2 by weight. Although not necessary, the reaction may be conducted in the presence of an inert solvent.

In the present aspect of the invention, there is provided a composition of matter comprising a novel alpha-enol ether compound having the formula

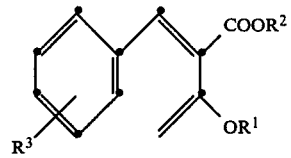

wherein $R^1$ is ($C_1$–$C_{12}$)alkyl, ($C_6$–$C_{20}$)aryl, or ($C_7$–$C_{21}$)alkylaryl or aralkyl;

$R^2$ is ($C_1$–$C_{12}$)alkyl; and $R^3$ is halo, carboxy or ($C_1$–$C_{12}$)alkyl, alkoxy, acyl, acyloxy, carbalkoxy or alkylthio.

The alpha-enol ethers of the invention may be substituted in the ortho, ortho or para position of the aromatic ring with respect to the carboxy-containing substituent. A preferred group of alpha-enol ethers of the invention is that wherein substituent $R^3$ of the aromatic ring is in the ortho or para position, and more preferably in the para position. Preferred $R^3$ substituents are alkyl such as methyl, ethyl or isopropyl, halo such as chlorine or bromine, carboxy, acyl such as acetyl, and alkoxy such as methoxy or ethoxy.

Another group of preferred alpha-enol ethers of the invention are those wherein the $R^1$ substituent is ($C_1$–$C_5$)alkyl, ($C_6$–$C_{10}$)aryl or ($C_7$–$C_{11}$)alkylaryl or aralkyl, and even more preferred is a group of alpha-enol ethers wherein the $R^2$ substituent is methyl, since most of the methyl ether derivatives are volatile and therefore easier to isolate than the higher alkyl or aryl esters.

Still another group of preferred alpha-enol ethers of the invention are those wherein the $R^3$ substituent is $(C_1-C_3)$alkyl, and more preferably methyl.

The alpha-enol ethers of the invention can be prepared by heating an alkylene or dialkyl ketal of an alpha-acetyl cinnamic acid or ester thereof at a temperature of about 75° to 250° C., and more preferably about 125° C., or by distilling the ketal, as described in the pending U.S. application Ser. No. 107,744 by the present inventors, described above.

Having now generally described this invention the same will be better understood by reference to certain specific examples, which are included herein for purposes of illustration only and are not intended to be limiting of the invention or any embodiment thereof unless so specified.

EXAMPLES

EXAMPLE 1

SYNTHESIS OF THE DIMETHYL KETAL OF METHYL P-ISOPROPYL ALPHA-ACETYL CINNAMATE WITHOUT AN ISOMERIZATION CATALYST

This example demonstrates the utility of a process in which a ketal is generated in the absence of an isomerization catalyst.

A solution of 12.30 grams (0.050 moles) of methyl p-isopropyl alpha-acetyl cinnamate in 30 mL of 1/1 trimethyl orthoformate/methanol is prepared in a 50 mL round-bottom flask provided with a thermometer, a gas inlet and an exit for the gas. To this solution are added 1.3 grams of an acidic resin, e.g., Amberlyst-15 ®, and then a slow steady stream of nitrogen is established through the solution. The solution is then heated to 55° C. and maintained at that level for 6.5 hours. The solution is then filtered, swirled with about 1 gram of a slightly basic resin, e.g., Amberlyst-21 ®, to remove any remaining acid and filtered again. The solvent is then removed in a vacuo to give 14.12 grams of crude dimethyl ketal. The identity of the ketal is established on the basis of its spectral properties which are listed below.

| 400 MHz NMR (CDCl3): | delta = 1.23(d,6H), |
| --- | --- |
| | 1.62(s,3H), |
| | 2.83-2.96(m,1H), |
| | 3.27(s,6H), 3.74(s,3H), |
| | 6.80(s,1H), |
| | 7.18(d,2H,J=9Hz), |
| | 7.23(d,2H,J=9Hz). |
| IR (neat): | 1729, 1210, 1055 cm$^{-1}$. |
| Exact Mass $C_{16}H_{14}O_4$: | |
| Calculated: | 292.1668. |
| Found: | 292.1676. |

EXAMPLE 2

SYNTHESIS OF DIMETHYL KETAL OF METHYL P-ISOPROPYL ALPHA-ACETYL CINNAMATE WITH ISOMERIZATION CATALYST

This example demonstrates the overall process using an isomerization catalyst to assit in the generation of a ketal.

A solution of 12.30 grams (0.0500 moles) of methyl p-isopropyl alpha-acetyl cinnamate in 30 mL of 1/1 trimethyl orthoformate/methanol is prepared in a 50 mL round-bottom flask. To this solution are added 1.2 grams of an acidic resin, e.g., Amberlyst-15 ®, and 10 mg (11 micromoles) of hydridocarbonyl tris(trisphenylphosphine)-rhodium. The mixture is stirred at room temperature for 5 to 6 hours and then filtered to remove the insoluble resin. The mixture is then swirled with 1 grams of a slightly basic resin, e.g., Amberlyst-21 ® resin, to neutralize any acidic impurities, filtered, and the solution reduced in volume in vacuo to give 13.83 grams of crude dimethyl ketal.

EXAMPLE 3

SYNTHESIS OF DIMETHYL ALPHA-ENOL ETHER METHYL P-ISOPROPYL ALPHA-ACETYL CINNAMATE

This example demonstrates the feasibility of isolating the enol ethers of methyl p-isopropyl alpha-acetyl cinnamate.

Using 24.6 grams (0.100 moles) of methyl p-isopropyl alpha-acetyl cinnamate, a sample of the crude dimethyl ketal is generated using the procedure of Example 1. After the reaction is complete and the mixture has been treated as described herein, the crude ketal is distilled using a short-path simple distillation at a pressure of 0.8 to 1.0 mmHg and a fraction boiling at 158° to 164° C. is obtained. Based on proton NMR spectra, the product is identified as a 1/1 mixture of two alpha-enol ether isomers which contains about 15% of the ketal as impurity. The product weighs 16.11 grams which represents a 62% yield of the enol ethers. The remaining material is left behind in the distillation flask as a glassy, polymeric solid. A description of the proton NRM of each, as deciphered from the mixture, is given below.

| 400 MHz for One Enol Ether Isomer: | delta = 1.23(d,3H), |
| --- | --- |
| | 2.80-2.95(m,1H), |
| | 3.69(s,3H), 3.77(s,3H), |
| | 4.21(s,2H), 7.10(s,1H), |
| | 7.20(d,2H,J=9Hz), |
| | 7.27(d,2H,J=9Hz). |
| 400 MHz NMR for the other Enol Ether Isomer: | delta = 1.25(d,6H), |
| | 2.80-2.95(m,1H), |
| | 3.70(s,3H), 3.81(s,3H), |
| | 4.20(s,1H,J=2.5Hz), |
| | 4.36(d,1H,J=2.5Hz), |
| | 7.23(d,2H,J=9Hz), |
| | 7.48(d,2H,J=9Hz), |
| | 7.69(s,1H). |

EXAMPLE 4

KETALIZATION OF METHYL P-METHYL ALPHA-ACETYL CINNAMATE

A solution of 10.90 grams (0.050 moles) of methyl alpha-acetyl cinnamate and 10 milligrams (11 micromoles) of hydridocarbonyl tris(phenyl)rhodium in 30 mL of 1/1 trimethyl orthoformate/methanol is prepared in a 50 mL round-bottom flask. To this solution are added 1 to 1.2 grams of an acidic resin, e.g., Amberlyst-15 ®, and the mixture is stirred at room temperature for 5 to 7 hours. The reaction mixture is then filtered to remove the resin, swirled with about 1 gram of a slightly basic resin, e.g., Amberlyst-21 ®, filtered again, washed with 1/1 trimethyl orthoformate/methanol and the solvent removed in vacuo. A sample is examined spectroscopically (NMR, IR, mass spec) to verify the identity of the ketal is found to contain a single isomer. There is always a small amount of the enol ether present whose identity is also confirmed by mass spectroscopy. The crude ketal weighs 12.92 grams. The spectroscopic data obtained are given below.

| 400 MHz Proton NMR (CDCl3): | delta = 1.62(s,3H), 2.33(s,3H), 3.26(s,6H), 3.72(s,3H), 6.18(s,1H), 7.12(d,2H,J=9Hz), 7.18(d,2H,J=9Hz). |
|---|---|
| IR (CH2Cl2): | 1736 cm$^{-1}$. |
| Mass Spectrum (m+/e): | 43, 89, 135, 233, 264. |
| Exact Mass C15H20O4: | |
| Calculated: | 264.1356. |
| Found: | 264.1345. |

EXAMPLE 5

KETALIZATION OF METHYL P-BROMO ALPHA-ACETYL CINNAMATE

A solution of methyl p-bromo alpha-acetyl cinnamate (mixture of olefin isomers, 14.15 grams, 0.050 moles), 15 mL of trimethyl orthoformate and 15 mL of methanol is prepared in a 50 mL round-bottom flask which is equipped with a thermometer inlet, a gas inlet consisting of a pipette connected to a nitrogen source and supported in a thermometer adaptor, and a gas outlet. To this solution are added 1.2 grams of an acidic resin, e.g., Amberlyst-15 ®, and a slow, consistent inert gas purge is established through the solution. The solution is stirred magnetically and maintained at a temperature of 55° C. for a period of 5.5 hours. The material is then filtered, neutralized by swirling the mixture with a slightly basic resin, e.g., Amberlyst-21 ®, and the solvent is removed in vacuo. The crude ketal weighs 16.42 grams. The spectral properties of the compound are listed below.

| 400 MHz Proton NMR (CDCl3): | delta = 1.61(s,3H), 3.26(s,6H), 3.71(s,3H), 6.79(s,1H), 7.15(d,2H,J=9Hz), 7.44(d,2H,J=9Hz). |
|---|---|
| IR (CH2Cl2): | 1729 cm$^{-1}$. |
| Mass Spectrum (m+/e): | 89, 158, 199, 201, 297, 299, 313, 315, 328, 2330. |
| Exact Mass C14H17BrO3: | |
| Calculated: | 328.0306. |
| Found: | 328.0304. |

EXAMPLE 6

KETALIZATION OF METHYL P-CARBOMETHOXY ALPHA-ACETYL CINNAMATE

To a 1-L 3-neck flask equipped with a mechanical stirrer, Dean-Stark trap, dry ice condenser and temperature controller is added methyl p-carbomethoxy alpha-acetyl cinnamate (125 g, 0.48 mol), trimethyl orthoformate (125 mL), an acidic resin, e.g., Amberlyst-15 ®, (5 g) and methanol (125 mL). the mixture is heated at 50° to 60° C. for 1.5 hours or until the theoretical amount (30 mL) of methyl formate is collected. The mixture is filtered to remove the resin and stored overnight at −20° C. The product crystallizes as a cake. The mother liquor is decanted and the product is transferred to a large beaker where it is broken up and washed with cold methanol (100 mL). The product is then air dried. The yield is 100 g (68%). Melting Point: 64° to 66° C. The data corresponding to this product are given below.

| Analysis of C16H20O6: | |
|---|---|
| Calculated: | C,62.34; H,6.49. |
| Found: | C,63.32; H,5.40. |
| 400 MHz H NMR (CDCl3): | delta = 1.63(s,3H), 3.27(s,6H), 3.70(s,3H), 3.92(s,3H), 7.00(s,1H), 7.35(d,2H,J=9Hz), 7.98(d,2H,J=9Hz) |
| Mass Spectrum (m+/e): | 308, 277, 179, 89. |
| IR: | vCO at 1720 cm$^{-1}$ (strong). |

The invention now being fully described, it will be apparent to one of ordinary skill in the art that many changes and modifications can be made thereto without departing from the spirit or scope of the invention as set forth herein.

What is claimed is:

1. An alkylene or dialkyl ketal of the formula

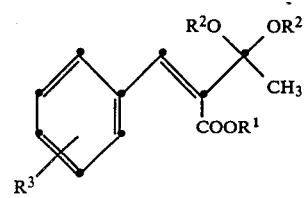

wherein
R$^1$ is C$_1$–C$_{12}$)alkyl, (C$_6$–C$_{20}$)aryl or (C$_7$–C$_{20}$)alkylaryl or aralkyl;
R$^2$ is (C$_1$–C$_{12}$)alkyl or the two R$^2$ taken together are (C$_2$–C$_{12}$)alkylene; and
R$^3$ is halo, carboxy or (C$_1$–C$_{12}$)alkyl, alkoxy, acyl, acyloxy, carbalkoxy or alkylthio.

2. The ketal of claim 1, wherein R$^3$ is in the para position.
3. The ketal of claim 1, wherein R$^3$ is isopropyl.
4. The ketal of claim 1, wherein R$^3$ is chlorine or bromine.
5. The ketal of claim 1, wherein R$^3$ is carboxy.
6. The ketal of claim 1, wherein R$^3$ is acetyl.
7. The ketal of claim 1, wherein R$^3$ is methyl.
8. The ketal of claim 1, wherein R$^2$ is (C$_1$–C$_3$)alkyl.
9. The ketal of claim 8, wherein R$^2$ is methyl.
10. The ketal of claim 1, wherein R$^1$ is (C$_1$–C$_3$)alkyl.
11. The ketal of claim 10, wherein R$^1$ is methyl.
12. An alpha-enol ether of the formula

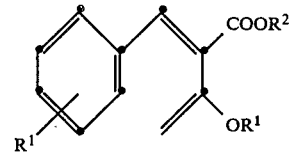

wherein
R$^1$ is (C$_1$–C$_{12}$)alkyl, (C$_6$–C$_{20}$)aryl or (C$_7$–C$_{21}$)alkylaryl or aralkyl;

$R^2$ is $(C_1-C_{12})$alkyl; and $R^3$ is halo, carboxy or $(C_1-C_{12})$alkyl, alkoxy, acyl, acyloxy, carbalkoxy or alkylthio.

13. The enol ether of claim 12, wherein $R^3$ is in the para position.

14. The enol ether of claim 12, wherein $R^3$ is isopropyl.

15. The enol ether of claim 12, wherein $R^3$ is chlorine or bromine.

16. The enol ether of claim 12, wherein $R^3$ is carboxy.

17. The enol ether of claim 12, wherein $R^3$ is acetyl.

18. The enol ether of claim 12, wherein $R^3$ is methyl.

19. The enol ether of claim 11, wherein $R^2$ is $(C_1-C_3)$alkyl.

20. The enol of claim 17, wherein $R^2$ is methyl.

21. The enol ether of claim 19, wherein $R^1$ is $(C_1-C_3)$alkyl.

* * * * *